(12) United States Patent
Varadharajulu

(10) Patent No.: US 7,186,024 B2
(45) Date of Patent: Mar. 6, 2007

(54) TABLE CONTROL METHOD, PATIENT SUPPORTING DEVICE, AND X-RAY IMAGING APPARATUS

(75) Inventor: Muthuvelan Varadharajulu, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 70 days.

(21) Appl. No.: 10/964,309

(22) Filed: Oct. 12, 2004

(65) Prior Publication Data

US 2005/0084074 A1    Apr. 21, 2005

(30) Foreign Application Priority Data

Oct. 21, 2003    (JP) ............................. 2003-360467

(51) Int. Cl.
*A61B 6/04* (2006.01)
(52) U.S. Cl. ............................. 378/209; 5/509.1; 5/607
(58) Field of Classification Search .................... 378/4, 378/17, 20, 208, 209, 210; 5/600, 607, 509.1, 5/601
See application file for complete search history.

(56) References Cited

U.S. PATENT DOCUMENTS

| 3,980,288 | A |   | 9/1976  | Mitchell et al. |         |
|-----------|---|---|---------|-----------------|---------|
| 4,197,465 | A |   | 4/1980  | Schneider       |         |
| 4,481,657 | A | * | 11/1984 | Larsson         | 378/209 |
| 4,484,343 | A |   | 11/1984 | Cesar           |         |
| 4,503,844 | A |   | 3/1985  | Siczek          |         |
| 4,550,421 | A |   | 10/1985 | Louiday         |         |
| 4,674,107 | A | * | 6/1987  | Urban et al.    | 378/98  |
| 5,425,069 | A | * | 6/1995  | Pellegrino et al.| 378/198|
| 5,475,885 | A |   | 12/1995 | Ishikawa        |         |
| 5,490,296 | A | * | 2/1996  | Fleury et al.   | 5/601   |
| 5,825,843 | A | * | 10/1998 | Kobayashi       | 378/20  |
| RE36,415  | E |   | 11/1999 | McKenna         |         |
| 6,237,707 | B1| * | 5/2001  | Lyke et al.     | 180/19.3|
| 6,574,808 | B1| * | 6/2003  | Brown et al.    | 5/601   |
| 2002/0104163 | A1 | * | 8/2002 | Reimann     | 5/601   |
| 2004/0261176 | A1 |   | 12/2004 | Plannerer  |         |
| 2004/0261177 | A1 | * | 12/2004 | Hoth et al. | 5/601   |

FOREIGN PATENT DOCUMENTS

| JP | 63-73936   |   | 4/1988 |
|----|------------|---|--------|
| JP | 05-004150  | * | 1/1993 |
| JP | 05004150   |   | 1/1993 |
| JP | 2002-177263| * | 6/2002 |

OTHER PUBLICATIONS

French Search Report, FA659171, FR041150, Apr. 28, 2005, 1 pg.
English language translation of Japanese patent No. 63-73936.

* cited by examiner

*Primary Examiner*—Edward J. Glick
*Assistant Examiner*—Anastasia S. Midkiff
(74) *Attorney, Agent, or Firm*—Carl B. Horton, Esq.; Armstrong Teasdale LLP

(57) ABSTRACT

A table control method for controlling a tabletop driven out of a base in the horizontal direction, wherein deflection of a tip of the tabletop due to load is compensated by tilting the tabletop to lift the tip.

6 Claims, 4 Drawing Sheets

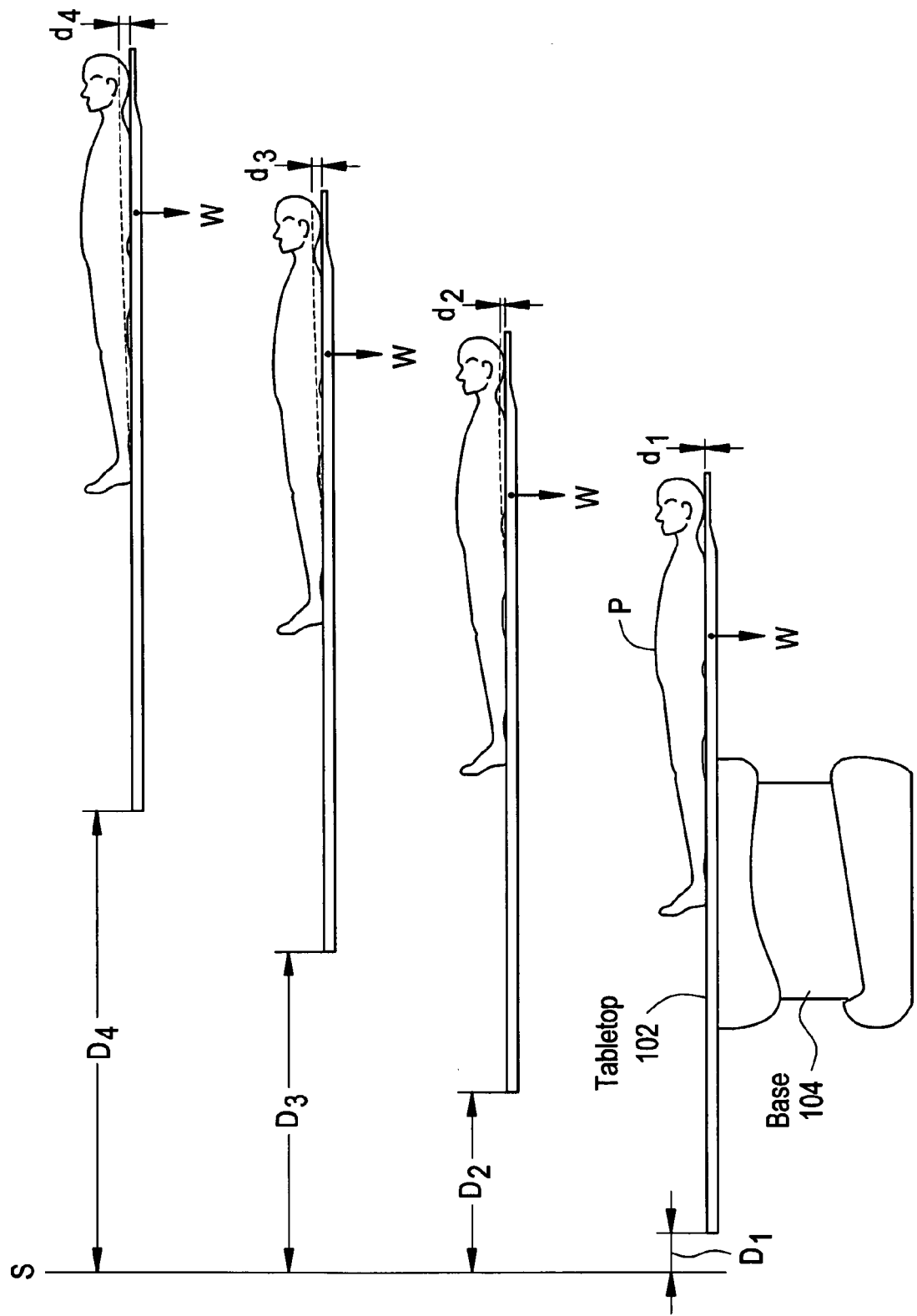

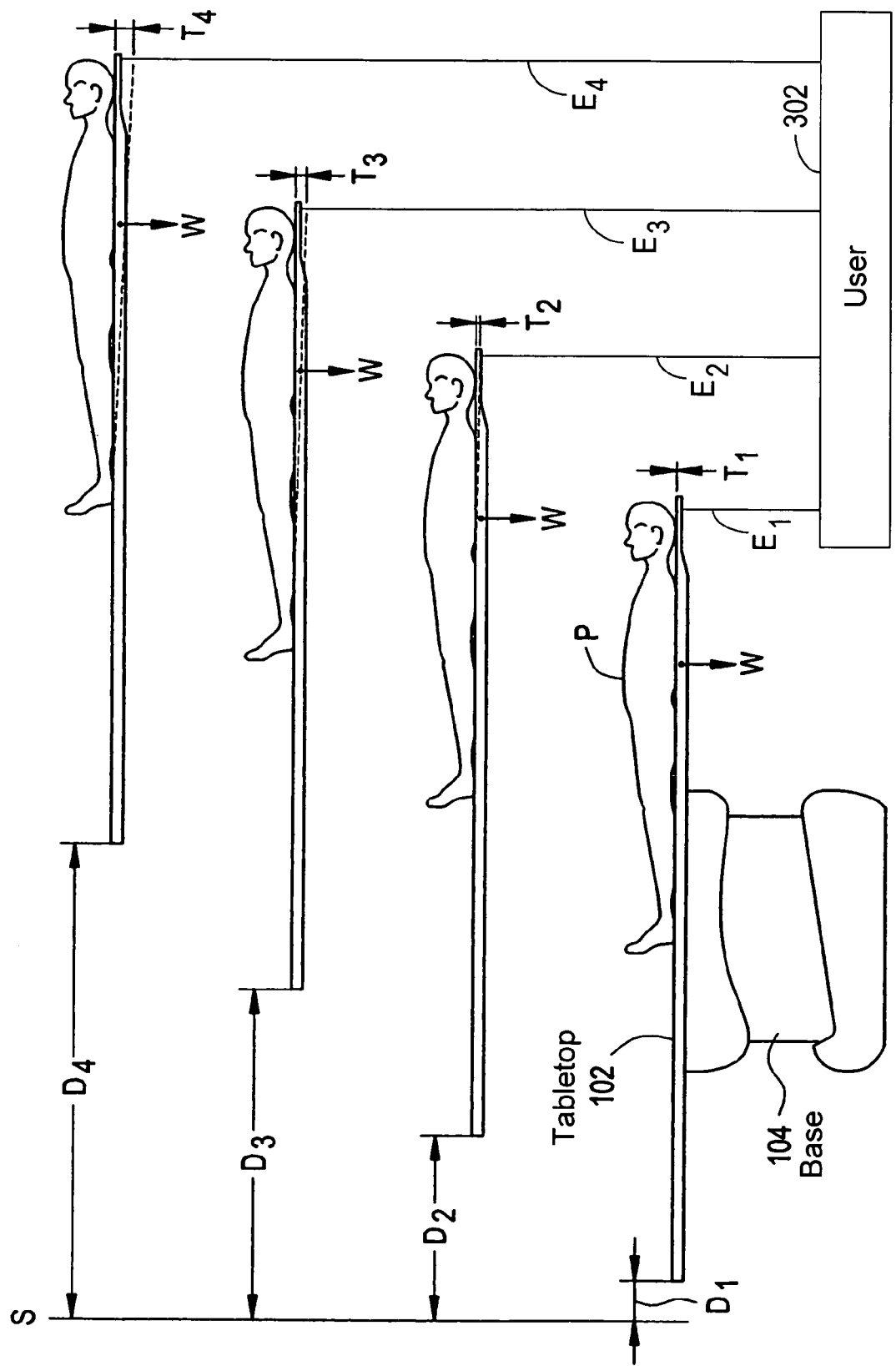

TABLE CONTROL METHOD, PATIENT SUPPORTING DEVICE, AND X-RAY IMAGING APPARATUS

CROSS REFERENCE TO RELATED APPLICATION

This application claims the benefit of Japanese Application No. 2003-360467 filed Oct. 21, 2003.

BACKGROUND OF THE INVENTION

The present invention relates to a table control method, a patient supporting device, and an X-ray imaging apparatus. More particularly, it relates to a method for controlling a tabletop driven out of a base in the horizontal direction, a patient supporting device having such a tabletop, and an X-ray imaging apparatus having such a patient supporting device.

X-ray imaging apparatuses use a patient supporting device for supporting a patient laying on the supporting device. Some of patient supporting devices are so designed that a tabletop can be driven out of a base in the horizontal direction. (Refer to Patent Document 1, for example.)

[Patent Document 1] Japanese Unexamined Patent Publication No. 2002-177263 (FIGS. 5 and 6 on pages 2 to 3)

A tabletop driven out is deflected due to load. Deflection of the tabletop is increased with increase in amount of driving and with increase in load. If a tabletop is so designed that the user manually moves the tabletop to adjust radiographic positions, a problem arises. As deflection of the tabletop is increased, the resistance in it is increased as well, and it becomes more difficult to manually operate.

SUMMARY OF THE INVENTION

Therefore, an object of the present invention is to provide a table control method wherein a tabletop can be easily moved by hand regardless of its deflection, a patient supporting device which exercises such control, and an X-ray imaging apparatus having such a patient supporting device.

(1) According to an aspect of the means for solving the above problem, the present invention is a method for controlling a tabletop driven out of a base in the horizontal direction, characterized in that deflection of the tip of the tabletop due to load is compensated by tilting the tabletop to lift the tip.

(2) According to another aspect of the means for solving the above problem, the present invention is a patient supporting device having a tabletop which is driven out of a base in the horizontal direction, characterized in that the supporting device comprises a compensating means which compensates deflection of the tip of the tabletop due to load by tilting the tabletop to lift the tip.

(3) According to another aspect of the means for solving the above problem, the present invention is an X-ray imaging apparatus having a supporting means which supports a patient on a tabletop driven out of a base in the horizontal direction, and an imaging means which takes radiographs of a patient utilizing X-rays, characterized in that the imaging apparatus comprises a compensating means which compensates deflection of the tip of the tabletop by tilting the tabletop to lift the tip.

In terms of the improvement of operability, it is preferable that the amount of lift of the tip should be determined based on the amount of displacement of the tabletop, the load on the tabletop, and the user's allowable effort. It is preferable that the amount of lift of the tip should be determined by the following expression:

$$T=2.38-0.00247D-1.16E+0.000022W^2+\\0.000003D^2-0.0135E^2+0.000028WD-\\0.000157DE+0.00301EW$$

where, D is the amount of displacement; W is the load; and E is the allowable effort.

This is preferable in terms of the further improvement of operability. It is preferable that the E should be determined by the following expression:

$$E=1.72 \text{ kg}+(0.00354 \text{ kg/mm}) D$$

where, D is the amount of displacement.

This is preferable in terms of the more further improvement of operability.

According to the above aspects of the present invention, deflection of the tip of a tabletop due to load is compensated by tilting the tabletop to lift the tip. Therefore, the tabletop can be easily moved by hand regardless of its deflection.

Further objects and advantages of the present invention will be apparent from the following description of the preferred embodiments of the invention as illustrated in the accompanying drawings.

BRIEF DESCRIPTION OF THE DRAWINGS

FIG. 3 is a drawing illustrating the way the tabletop is driven out.

FIG. 4 is another drawing illustrating the way the tabletop is driven out.

DETAILED DESCRIPTION OF THE INVENTION

Figure 1:
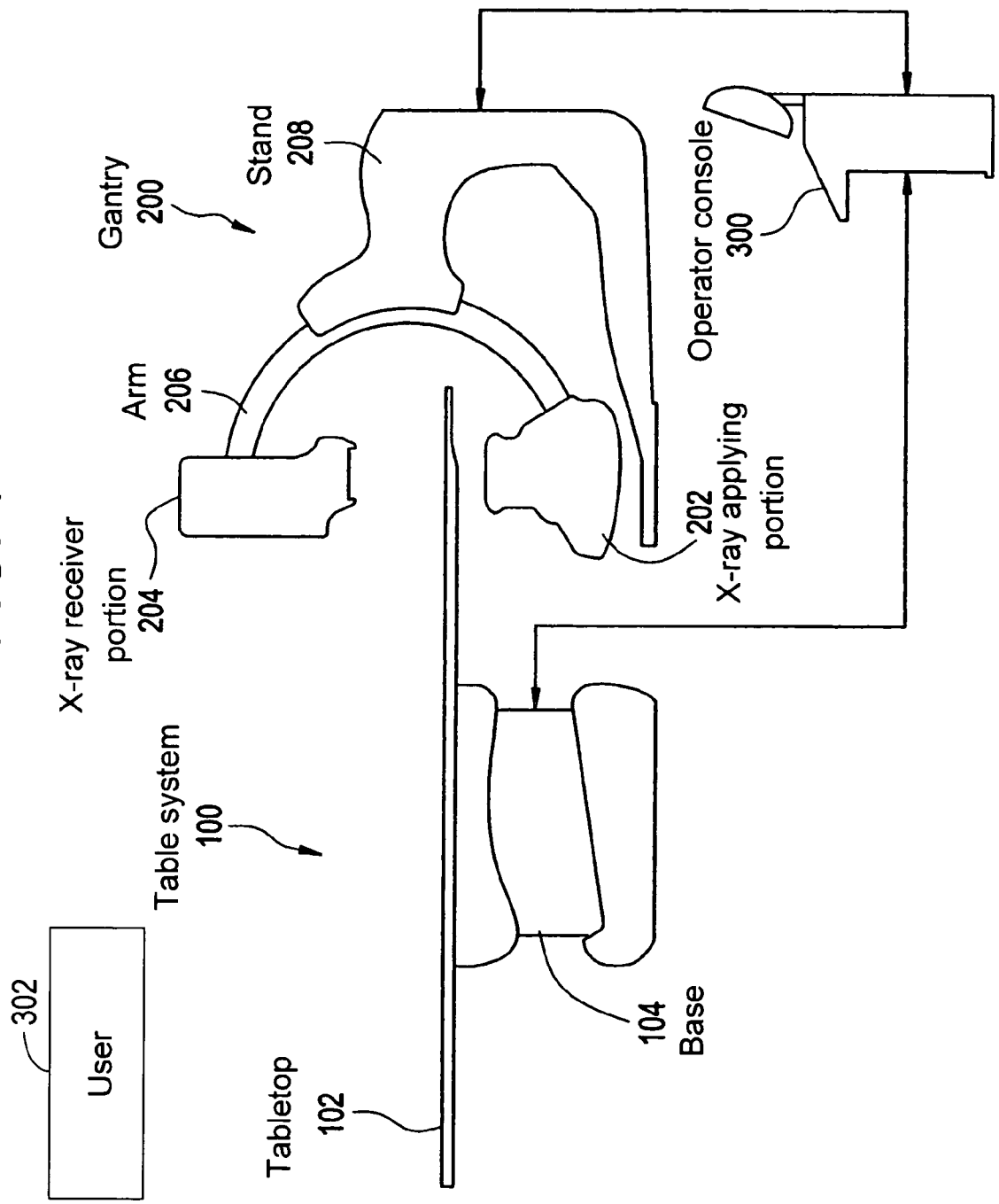
FIG. 1 is a drawing schematically illustrating the configuration of the X-ray imaging apparatus.

Referring to drawings, the best mode for carrying out the invention will be described in detail below. FIG. 1 schematically illustrates the configuration of the X-ray imaging apparatus. This apparatus is an example of the best mode for carrying out the present invention. The configuration of this apparatus illustrates an example of the best mode with respect to the X-ray imaging apparatus according to the present invention.

As illustrated in the figure, this apparatus comprises a table system 100, a gantry 200, and an operator console 300. The table system 100 is an example of the supporting means according to the present invention. The gantry 200 is an example of the imaging means according to the present invention.

The table system 100 has a tabletop 102. The tabletop 102 is supported on a base 104. The tabletop 102 is horizontal when it is in normal state. The tabletop 102 is an example of the tabletop according to the present invention. The base 104 is an example of the base according to the present invention.

In the gantry 200, an X-ray applying portion 202 and an X-ray receiving portion 204 which are opposed to each other are supported on an arc-shaped arm 206. The arm 206 is supported on a stand 208.

The X-ray applying portion 202 incorporates an X-ray tube, and projects X-rays toward the X-ray receiving portion 204. The X-ray receiving portion 204 incorporates a photo detector, such as an image intensifier, and receives X-rays projected by the X-ray applying portion 202.

The operator console 300 is a man-machine interface for a user 302. The operator console 300 comprises information processing equipment, such as computer, and its peripheral devices. The operator console 300 controls the table system 100 and the gantry 200 according to instructions from the user 302, and thereby takes radiographs.

Figure 2:
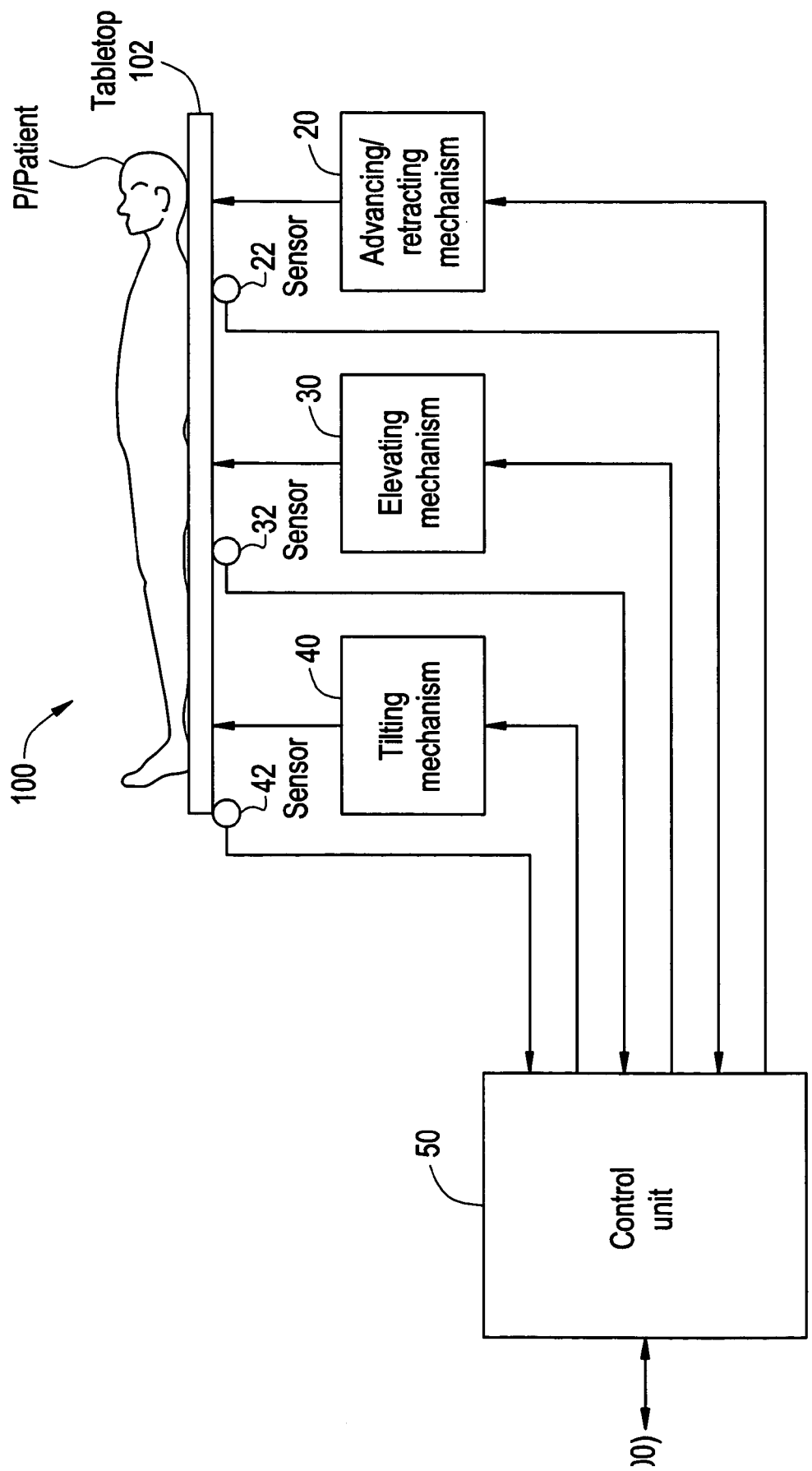
FIG. 2 is a block diagram of the table system.

FIG. 2 is a block diagram of the table system 100. The table system 100 is an example of the best mode for carrying out the present invention with respect to the patient supporting device. The configuration of this system illustrates an example of the best mode with respect to the patient supporting device according to the present invention. The motion of this system illustrates an example of the best mode with respect to the table control method according to the present invention.

As illustrated in the figure, a patient P is placed on the tabletop 102 in face up position. The tabletop 102 is driven by an advancing/retracting mechanism 20, an elevating mechanism 30, and a tilting mechanism 40. The advancing/retracting mechanism 20 is capable of moving forward/backward the tabletop in the direction of the length (the direction of the body axis of the patient); the elevating mechanism 30 is capable of moving up/down the tabletop in the vertical direction; and the tilting mechanism 40 is capable of tilting the tabletop relative to the horizontal direction. Advancing/retracting, moving up/down, and tilting of the tabletop 102 are detected by respective sensors 22, 32, and 42.

The advancing/retracting mechanism 20, elevating mechanism 30, tilting mechanism 40 are controlled by a control unit 50. Detection signals from the sensors 22, 32, and 42 are inputted to the control unit 50. For the control unit 50, for example, a microcomputer is used. The advancing/retracting mechanism 20, elevating mechanism 30, tilting mechanism 40, and control unit 50 are housed in the base 104.

FIG. 3 illustrates the way the tabletop 102 is advanced and retracted. As illustrated in the figure, the tabletop 102 is driven out of the base 104 in the direction of the body axis of the patient P. The figure shows four states different in the amount of displacement from reference position S. Letting the amounts of displacement in these states be D1, D2, D3, and D4, respectively, D1<D2<D3<D4.

The tabletop 102 is deflected under the load W arising from the weight of the patient, and its tip sags. The amount of deflection will be defined as the distance by which the tip of the tabletop descends relative to no-deflection state (indicated by broken lines). Then, the amount of deflection is increased with increase in amount of displacement. Thus, letting the amounts of deflection in the four states be d1, d2, d3, and d4, respectively, d1<d2<d3<d4.

Such deflection of the tip of the tabletop 102 increases the resistance in the tabletop 102 when the user 302 attempts to move the tabletop 102 by hand, and this makes the tabletop difficult to operate. This resistance is increased with increase in the amount of deflection; therefore, manual operation become more difficult with increase in the amount of displacement.

In the patient supporting device according to the present invention, deflection of the tabletop 102 is compensated to cope with this. Deflection compensation is carried out by tilting the tabletop 102 to lift its tip. FIG. 4 illustrates the tabletop with its deflection compensated. As illustrated in the figure, the tabletop 102 is tilted so that the tip of the tabletop 102 will be lifted by distances T1, T2, T3, and T4, respectively, in the four states. The amounts T1, T2, T3, and T4 of lift correspond to the amounts d1, d2, d3, and d4 of deflection, respectively.

Deflection compensation through tilting of the tabletop 102 is carried out by controlling the tilting mechanism 40 by the control unit 50. The control unit 50 and the tilting mechanism 40 are an example of the compensating means according to the present invention. The control unit 50 computes an amount of lift based on the amount of displacement and the load. Then, the control unit 50 tilts the tabletop 102 so that the amount of lift of the tip of the tabletop 102 will be matched with the computed amount of lift. In this computation of amount of lift, the effort which the user 302 allowably expend when the user 302 manually moves the tabletop 102 is also taken into account. Allowable effort of the user 302 is equivalent to the resistance the user 302 can afford to feel.

An example of an expression for computing amount T of lift (mm) is as follows:

$$T=2.38-0.00247D-1.16E+0.000022W^2+0.000003D^2-0.0135E^2+0.000028WD-0.000157DE+0.00301EW$$

where,

D: Amount of displacement (mm)
W: Load (kg)
E: allowable effort (kg) of the user 302.

The amount D of displacement is measured by the sensor 20. With respect to load W, a previously measured value is given through the operator console 300. Allowable effort E of the user 302 is determined by the following expression:

$$E=1.72 \text{ kg}+(0.00354 \text{ kg/mm}) D$$

Amounts of the user 302's allowable effort are E1, E2, E3, and E4 corresponding to the amounts of displacements D1, D2, D3, and D4, respectively.

Instead of determining E by the above expression, a constant value independent of the amount D of displacement may be taken for E.

By carrying out the above-mentioned deflection compensation, the user 302 can move the tabletop 102 by hand, feeling appropriate resistance, regardless of deflection of the tabletop 102. That is, the user 302 can easily move the tabletop 102 by hand.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A table control method for controlling a tabletop driven out of a base in the horizontal direction, wherein deflection of a tip of the tabletop due to a load is compensated by tilting the tabletop to lift the tip, wherein an amount of the lift of the tip is determined based an effort made by a user to move the tabletop, wherein the amount of lift of said tip is determined based on an amount of displacement of the tabletop and the load on the tabletop, and wherein letting said amount of displacement be D, said load be W, and said allowable effort be E, the amount of lift of said tip is expressed as follows:

$$T=2.38-0.00247D-1.16E+0.000022W2+0.000003D2-0.0135E2+0.000028WD-0.000157DE+0.00301EW.$$

2. The table control method according to claim 1, wherein said E is expressed as follows:

$$E=1.72+0.00354D.$$

3. A patient supporting device including a tabletop which is driven out of a base in the horizontal direction, wherein the patient supporting device comprises a compensating section which compensates deflection of a tip of the tabletop due to a load by tilting the tabletop to lift the tip, wherein said compensating section determines an amount of the lift of the tip based on an effort made by a user to move the tabletop, wherein said compensating section determines the amount of lift of said tip based on an amount of-displacement of the tabletop and the load on the tabletop, and wherein letting said amount of displacement be D, said load be W, and said allowable effort be E, the amount of lift of said tip is expressed as follows:

$$T=2.38-0.00247D-1.16E+0.000022W^2+0.000003D^2-0.0135E^2+0.000028WD-0.000157DE+0.00301EW.$$

4. The patient supporting device according to claim 3, wherein said E is expressed as follows:

$$E=1.72+0.00354D.$$

5. An X-ray imaging apparatus comprising: a supporting section which supports a patient on a tabletop driven out of a base in the horizontal direction; and an imaging section which takes radiographs of a patient utilizing X-rays, wherein the X-ray imaging apparatus further comprises a compensating section which compensates deflection of a tip of the tabletop due to a load by tilting the tabletop to lift the tip, wherein said compensating section determines an amount of the lift of the tip based on an effort made by a user to move the tabletop, wherein said compensating section determines the amount of lift of said tip based on an amount of displacement of the tabletop and the load on the tabletop, and wherein letting said amount of displacement be D, said load be W, and said allowable effort be E, the amount of lift of said tip is expressed as follows:

$$T=2.38-0.00247D-1.16E+0.000022W^2+0.000003D^2-0.0135E+0.000028WD-0.000157DE+0.00301EW.$$

6. The X-ray imaging apparatus according to claim 5, wherein said E is expressed as follows:

$$E=1.72+00354D.$$

\* \* \* \* \*

UNITED STATES PATENT AND TRADEMARK OFFICE
CERTIFICATE OF CORRECTION

PATENT NO. : 7,186,024 B2  Page 1 of 1
APPLICATION NO. : 10/964309
DATED : March 6, 2007
INVENTOR(S) : Varadharajulu It is certified that error appears in the above-identified patent and that said Letters Patent is hereby corrected as shown below:

In Claim 1, column 4, beginning at line 65, delete
"$T = 2.38 - 0.00247D - 1.16E + 0.000022W2 + 0.000003D2 - 0.0135E2 + 0.000028WD - 0.000157DE + 0.00301EW.$"
and insert therefor
-- $T = 2.38 - 0.00247D - 1.16E + 0.000022W^2 + 0.000003D^2 - 0.0135E^2 + 0.000028WD - 0.000157DE + 0.00301EW.$ --.

In Claim 5, column 6, beginning at line 16, delete
"$T = 2.38 - 0.00247D - 1.16E + 0.000022W^2 + 0.000003D^2 - 0.0135E + 0.000028WD - 0.000157DE + 0.00301EW.$"
and insert therefor
-- $T = 2.38 - 0.00247D - 1.16E + 0.000022W^2 + 0.000003D^2 - 0.0135E^2 + 0.000028WD - 0.000157DE + 0.00301EW.$ --.

Signed and Sealed this

Sixth Day of November, 2007

JON W. DUDAS
*Director of the United States Patent and Trademark Office*